United States Patent [19]

Combs

[11] Patent Number: 4,812,294

[45] Date of Patent: Mar. 14, 1989

[54] SPECIMEN PROCESSING SYSTEM

[75] Inventor: John W. Combs, Baltimore, Md.

[73] Assignee: Automated Diagnostic Systems, Inc., Arlington, Va.

[21] Appl. No.: 20,530

[22] Filed: Mar. 2, 1987

Related U.S. Application Data

[63] Continuation of Ser. No. 834,545, Feb. 28, 1986, abandoned.

[51] Int. Cl.$^4$ .................. G01N 21/00; B04B 1/00
[52] U.S. Cl. ...................... 422/72; 422/100; 422/102; 436/45; 494/19
[58] Field of Search .................. 422/72, 102, 100, 64; 436/45, 180; 494/19

[56] References Cited

U.S. PATENT DOCUMENTS

| | | | |
|---|---|---|---|
| 3,850,368 | 11/1974 | Boeckeler | 494/19 X |
| 3,882,716 | 5/1975 | Beiman | 494/19 X |
| 4,104,831 | 8/1978 | Kobayashi | 494/19 X |
| 4,296,882 | 10/1981 | Kobayashi | 494/19 X |
| 4,632,908 | 12/1986 | Schultz | 422/72 X |

FOREIGN PATENT DOCUMENTS 160282  11/1985  European Pat. Off. .

Primary Examiner—Michael S. Marcus
Attorney, Agent, or Firm—Iver P. Cooper

[57] ABSTRACT

A specimen preparation unit having a plurality of interconnected compartments is automatically loaded onto a centrifuge rotor arm at a first rotor position. Each rotor arm has two indexing means for independently rotating the unit about either or both of two axes orthogonal to each other and to the rotor arm. The orientation of the unit with respect to the centrifugal force vector is changed in a predetermined manner so as to cause fluid flow between desired compartments even under conditions of microgravity. The unit is centrifuged in at least two different orientations with respect to the centrifugal force vector. As the fluids move between compartments, the specimen is prepared. After the multistep preparation process is completed, the unit is rotated to another rotor position at which the prepared specimen and/or the entire unit is removed. The centrifugal processing unit is capable of processing a plurality of specimen preparation unit in the same or a different manner. A plurality of the compartments of the specimen preparation unit are connected by force-sensitive valves which prevent reflux and which respond only to forces substantially exceeding gravity. The specimen preparation unit may provide for parallel processing of specimen aliquots.

6 Claims, 14 Drawing Sheets

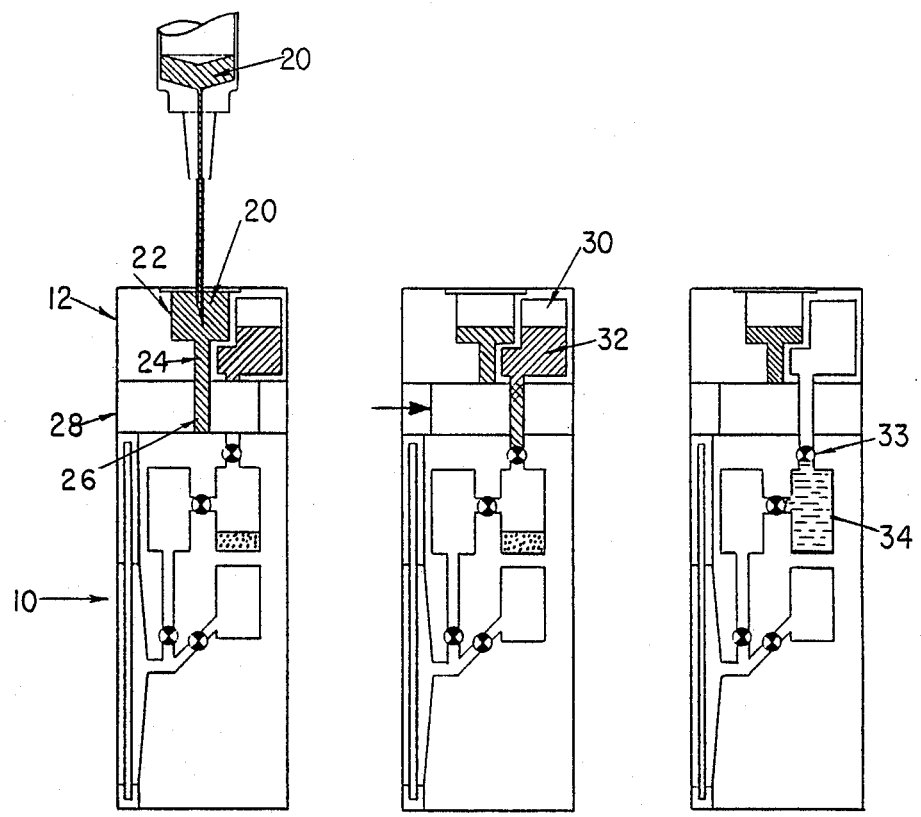
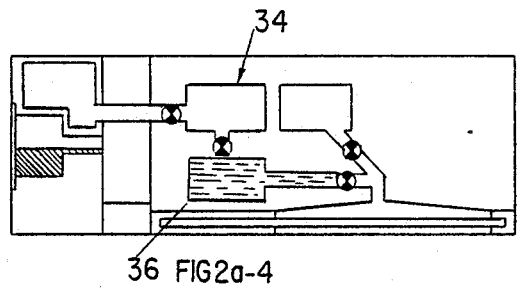
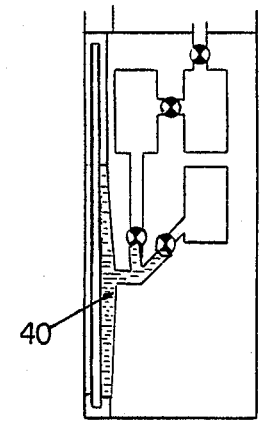
FIG. 2a-1    FIG. 2a-2    FIG. 2a-3
FIG. 2a-4
FIG. 2a
FIG. 2a-5

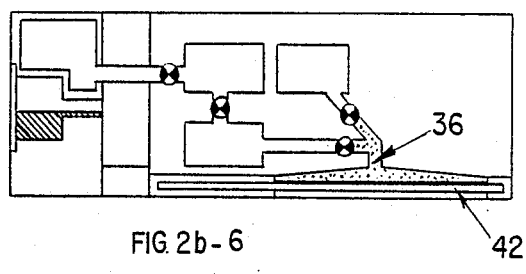
FIG. 2b-6
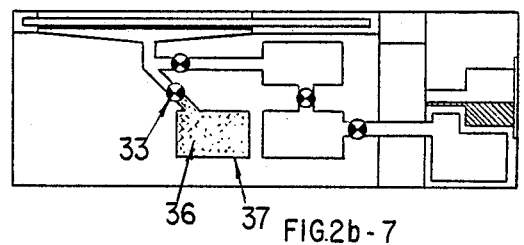
FIG. 2b-7
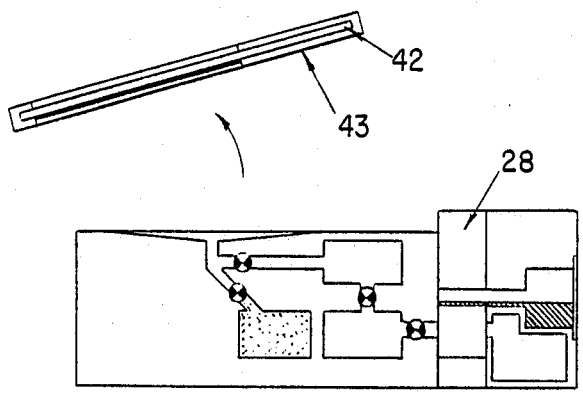
FIG. 2b-8
FIG. 2b.

46   48 FIG.3a-4

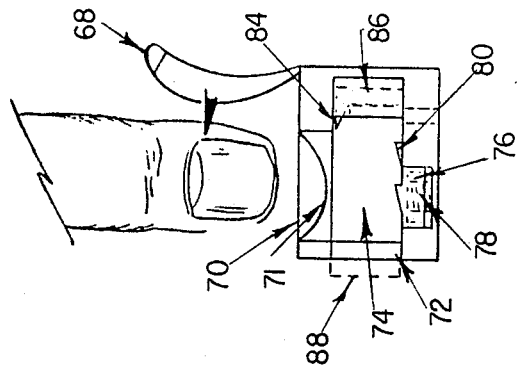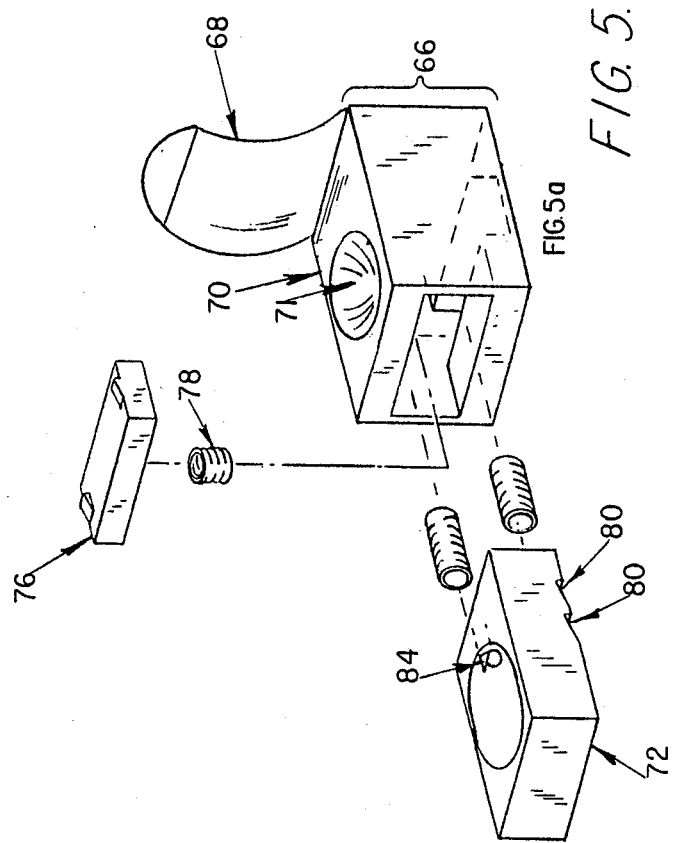

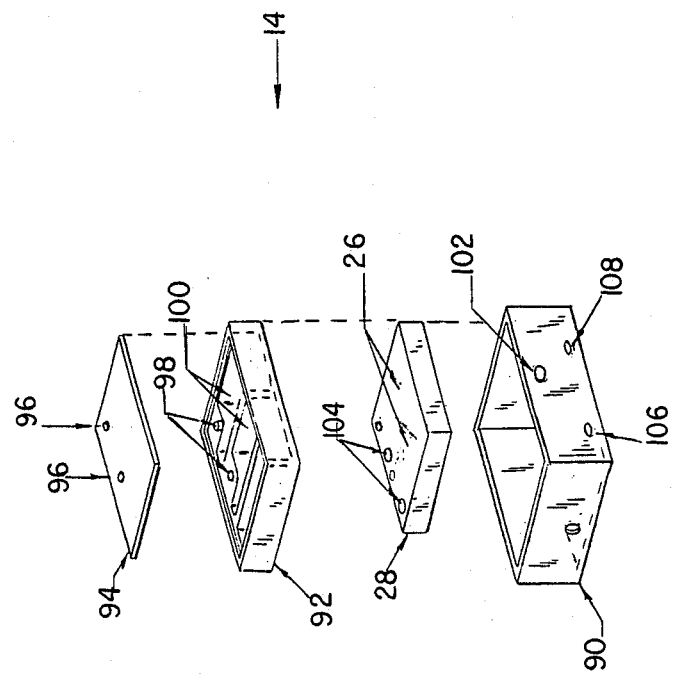

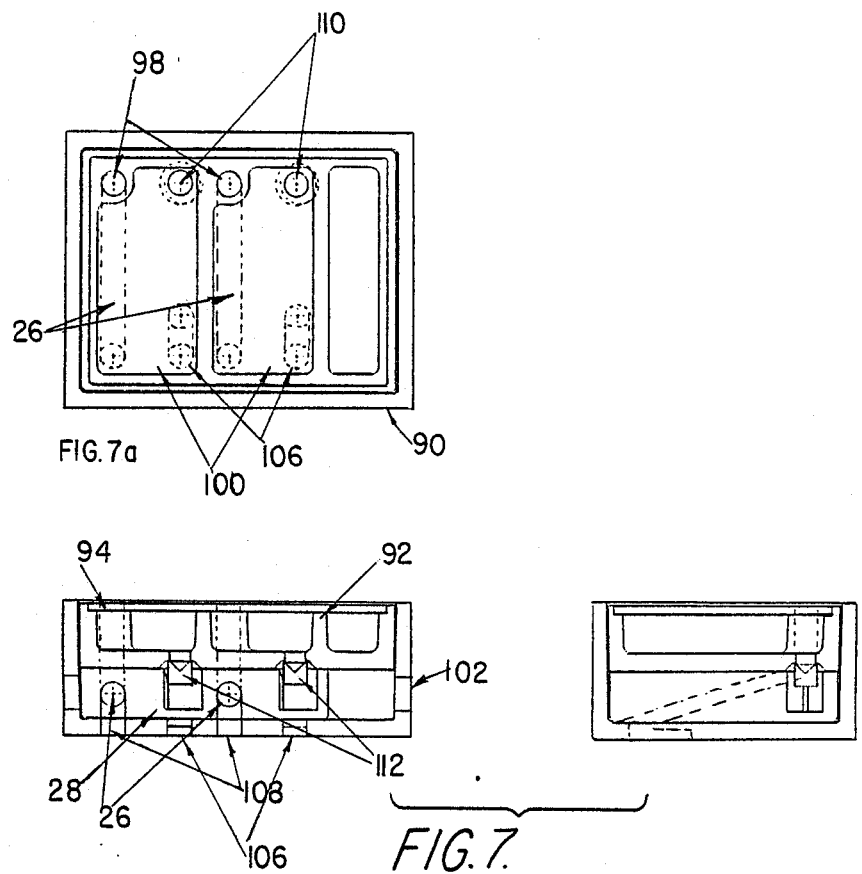

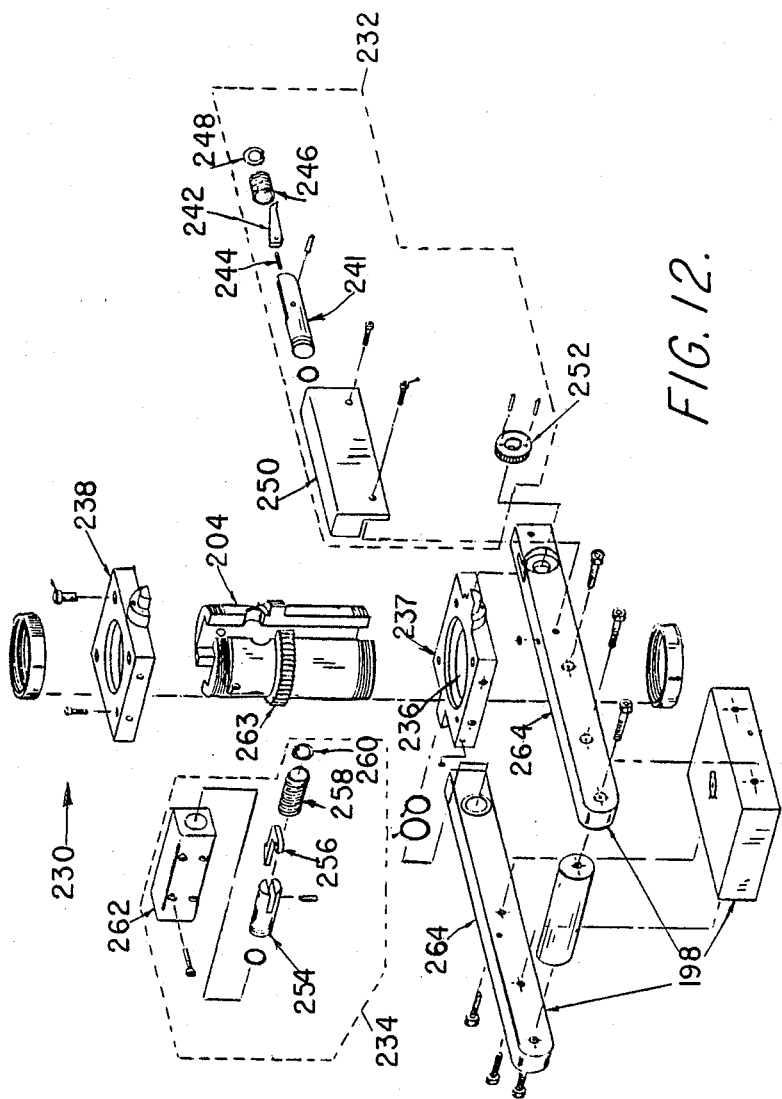

SPECIMEN PROCESSING SYSTEM

This application is a continuation of application Ser. No. 06/834,545, filed Feb. 28, 1986, now abandoned, the text of which is incorporated by reference herein.

BACKGROUND OF THE INVENTION

1. Field of the Invention

This invention relates to apparatus for laboratory specimen preparation, and in particular to such apparatus which operates automatically to process specimens in preparation for a plurality of physical chemical or biological tests, for quality control, etc. This apparatus will operate equally well in terrestrial or space (microgravity) environments. The apparatus comprises a multi-compartmented specimen preparation unit with force-sensitive valves and a centrifugal processing unit with means for locally rotating the former unit into any desired orientation with respect to the centrifugal force vector, about either of two axes.

2. Information Disclosure Statement

Currently, the standard mode for conducting tests on specimens such as human blood samples requires that these specimens be partially or wholly prepared by technicians in accordance with predetermined procedures by measuring aliquots, adding diluents, reagents, etc. It is often necessary to permit a specimen to incubate for a predetermined time and to be filtered as well as centrifuged. The number of individual steps necessary in order to prepare a particular specimen for testing can be large and the steps themselves can be complex and require special skills. Normally, a technician performs these steps in a laboratory setting. This procedure can take substantial time and is subject to human error.

It would, therefore, be beneficial to be able to prepare a specimen for testing without human intervention. To date, no single apparatus is known which can accurately and reliably process specimens in preparation for the multitude of testing procedures which are currently available, that can adapt to a wide panel of future testing procedures, and also operates independently of gravity. This independence is achieved by using centrifugal force to induce fluid flow in a particular direction within a freely orientable specimen processing unit.

Schultz, et al., Clin. Chem. 31(9): 1547 (1985) describe a system in which a multichambered test pack containing liquid reagents is subjected to alternating centrifugal fields, oriented at right angles to each other. The primary rotation is that of the centrifuge rotor, which causes the test pack to orbit the rotor axis. The test pack, which is essentially planar, lies in the plane of rotation of the rotor, and may be rotated secondarily about its own axis, perpendicular to the main face of the test pack and parallel to the rotor axis.

While it is thus possible to change the relative g-force vector within the test pack, there is no provision for rotating the test pack out of the plane of rotation of the rotor. If the test pack had a plurality of "vertical" (parallel to rotor axis) layers of compartments, it would not be possible to centrifugally transfer fluid between layers. In my device, each test pack may be rotated about two local axes as well as being revolved about the rotor axis.

Moreover, the test pack taught by Schultz is valveless. Thus, fluid may leak from one layer to another under gravitational influence. My test pack is equipped with force-sensitive valves, which will not be opened by gravitational forces alone.

Belman, U.S. Pat. No. 3,882,716 describes a centrifugal apparatus having centrifuge cells mounted at a fixed, acute angle to the drive shaft, each of these cells being rotatable about its own axis. This "satellite" rotation is intended to agitate the contents of the cell. At the lower end of each cell is a cuvette. Means are provided for bringing each cuvette into registry, sequentially, with a single read-out instrument. While the orbital position of the cells is controlled, no control is exercised over the rotational position of each cell and thereby over the local centrifugal force vector. Moreover, the cells have only one rotational degree of freedom.

Proni, U.S. Pat. No. 3,768,727 discloses another centrifugal analyzer in which sample columns are independently rotated about their own, fixed, substantially vertical axis.

Anderson, U.S. Pat. No. 3,586,484 describes a multistation analytical photometer. A central transfer disc initially holds precipitating solutions and sample solutions, separated by partitions. As the rotor spins, these solutions move to peripheral sedimentation chambers, and mix. When the rotor is returned to rest, supernatant drains into holding chambers. There is no provision for a specimen collecting and processing module which is separable from the rotor assembly, or for reorienting that module so that the centrifugal force applied by the rotor causes fluid to flow within the module in a different, non-coparallel direction. While the flow of supernatant in Anderson is in a direction perpendicular to the original flow of precipitant and sample, this second flow is induced by natural gravitational forces rather than by centrifugation. See also Klose, U.S. Pat. No. 4,557,600.

Guigan, U.S. Pat. No. 4,463,097 describes the use of centrifugal force to transfer sample from one compartment to another. These compartments are integral to the rotor assembly, and the compartments always receive the sample in the same sequence. The sample "zigzags" as it moves outward, the direction of rotation of the rotor being reversed at each step. The operability of the device is directly related to the special arrangement and connection of the compartments. See also Guigan, U.S. Pat. No. 4,519,981.

Curtis, U.S. Pat. No. 4,390,399 shows the combination of a test package with a spinning rotor for the purpose of chemical analysis. Pneumatically actuated barriers, flexible diaphragms, and rupturable seals are used to control and transport the sample from one compartment of the test package to the next in a programmed sequence. The direction of the centrifugal force with respect to the test package is constant throughout the sequence, that is, the rotor is used to induce flow in only one direction. The package has a fixed orientation with respect to the rotor.

Farina, U.S. Pat. No. 4,244,694 (FIG. 2) refers to a centrifugal analyzer in which test tubes are suspended by their rims in ball seats of the rotor assembly. When the rotor is spun, the test tubes swing out. There is no teaching, however, of using rotor speed to control the direction of flow of sample within the test tube.

Hardy, U.S. Pat. No. 4,092,113 places a blood sample device in the bucket of a conventional centrifuge. The bucket is swung out to a horizontal position when the rotor is start. The device comprises inner and outer sample vessels connected by a leakage path. There is no provision for reorienting the device so that the centrifugal force will induce fluid flow in another direction.

Aeschlimann, U.S. Pat. No. 4,236,666 describes a centrifuge with pivotable mounted magazines. This design is to facilitate positioning the magazines in either a slightly tilted "decanting" orientation or a generally horizontal "centrifuge" orientation.

Mochida, U.S. Pat. No. 4,479,720 discloses a rotor with a determinable angle of inclination, for increasing the rate of a reaction in tubes held by the rotor by increasing the contact area.

Sogi, U.S. Pat. No. 4,208,484 describes apparatus for automatically transferring a centrifuge tube to a centrifuge.

Anthon, U.S. Pat. No. 3,151,073 discloses a self-indexing centrifuge rotor.

DeGrave, U.S. Pat. No. 4,595,563 presents apparatus for sample transfer and analysis by centrifugation. Cuvette carriers are pivotably connected to the ends of the rotor arms. The apparatus is designed so that the inclination changes as the rotor speed is increased. Sample transfer takes place at one speed, and sample analysis at a higher speed.

Yamamoto, U.S. Pat. No. 4,632,808 relates to a chemical manipulator capable of automatically transporting a bucket between stations. The bucket may be moved in the x, y, or z directions. The manipulator is used to transfer the bucket to a centrifugal separator.

The disclosures of the above-identified patents are incorporated by reference.

SUMMARY OF THE INVENTION

One object of the present invention is to provide a system which is capable of accepting a specimen and performing all of the steps required to prepare the specimen for actual testing. These steps include aliquoting, the addition of diluents and reagents, filtering, incubating, centrifuging, applying uniform distributions of cellular specimens on microslides, etc.

Another object of the present invention is to provide a system for preparing a specimen in exactly the proper form for the test to be conducted whether it be in a vial, on a microslide, in a cuvette array, or on a "dry chemistry" film patch.

Another object of the present invention is to provide a system for preparing a specimen for testing which system includes the ability to automatically take a blood sample from a human being, measure a predetermined amount of blood, and process the blood for testing, thereby eliminating any need for human intervention.

Another object of the present invention is to provide, in a system for preparing a specimen, means for centrifugally processing the specimen.

Another object of the present invention is to provide, in a system for preparing a specimen, means for inducing the movement of the specimen (or aliquots thereof) through the system which functions independently of natural gravitational forces, so that the system may be used in a microgravity environment.

Another object of the invention is to provide for rotating the test pack independently about local axes so that the centrifugal force vector may assume any conceivable orientation with respect to the test pack, and without limiting the test pack to an essentially planar design.

Another object of the invention is to provide valves between compartments of the test pack so that fluid flow is prevented until the applied force exceeds a predetermined limit, which limit is greater than the force of gravity alone.

In accordance with the above and other objects, the present invention is a system for processing specimens, comprising a specimen preparation unit for receiving specimens to be processed, and a centrifugal processing unit for applying centrifugal force to the specimen preparation unit in a complex controlled sequence that accomplishes the preparation of the specimen. The specimen preparation unit comprises a self-contained, modular member preloaded with all the reagents and substrates required for specimen processing, and having a plurality of chambers, channels, valves, vents, fluid traps, filters, etc. At least one of said chambers contains fluid to be mixed with said specimen. The valves and channels are oriented such that fluid is induced flow sequentially between the chambers when the specimen preparation unit is subjected to centrifugal forces in a specified set of predetermined directions. This may include orienting the specimen preparation unit on any three dimensional axis, spinning for variable speeds and times, shifting the axis of spin during centrifugation, and more complex motions.

The centrifugal processing unit includes a mounting head for receiving the specimen preparation unit and automatically orienting and reorienting the specimen preparation unit in three dimensions with reference to the spin axis of the centrifuge, corresponding to the predetermined directions for inducing flow sequentially between the chambers.

In accordance with other aspects of the invention, the specimen preparation unit comprises a collection module having a sealed opening or a device for receiving or collecting a specimen, an adjacent aliquoting module for dividing and measuring predetermined amounts of the specimen, and an adjacent processing module for preparing the specimen for testing.

The collection module may include a device for the automatic extraction of a sample of blood from a human subject. The blood extracting device may include a mechanism for grasping an extension, such as a finger, of a human subject and a mechanism for puncturing the skin and obtaining a blood sample. The collection module may also embody a manifold that divides the specimen into one or more channels corresponding to a like number of processing channels in the aliquoting and processing modules. The number of such channels is determined by the particular test or tests for which specific specimen preparation units are adapted.

The aliquoting module may be single or multichannel. Each channel may be comprised of a chamber for storing a premeasured quantity of fluid to be mixed with the specimen, and a volumetric channel. The volumetric channel or channels are included in a sliding device that provides a predetermined amount of specimen, diluted in a premeasured quantity of fluid, to a first chamber of the processing module.

The aliquoting module may also include the structure for separately measuring and diluting a plurality of predetermined amounts of the specimen, and the processing module may include a plurality of parallel but different processing paths for simultaneously and separately processing each of the predetermined amounts of specimen.

It is not necessary that the specimen be in fluid form if it is to be collected, prepared and analyzed in the same compartment, the other compartments serving merely as holding areas for unstable reactants used in the preparative process.

In most cases, however, the specimen will be initially placed in one compartment and subsequently transported to another compartment at some state in the processing. For this purpose, the specimen, if not a fluid already, must be converted to fluid form. For purposes of these specifications and claims, the term "fluids" encompasses gases, liquids and viscous solids. A solid specimen may be converted to fluid form by dissolving or suspending it in a fluid, or by melting it. Similarly, solid reactants may be converted to fluid form when it is necessary to transport them within the specimen processing unit. Such "fluidizable substances" are also considered to be "fluids" for purposes of the appended claims.

The term "substances", as used in the appended claims, includes the specimen in its various states of preparation, chemicals which are reacted with each other, or with the specimen, and their reaction products, solvents, diluents, and other materials which play a role in specimen preparation or analysis, directly or indirectly, without limitation.

While the specimen of the Example is blood, the specimen may be another biological fluid, or a fluidizable biological tissue, or a specimen of a nonbiological character.

The present invention also may include a plurality of devices or substrates that receive the processed specimens and maintain them in a form ready for a variety of analyses. These devices or substrates are housed in a plurality of mounts for detachably holding the processed specimen devices or substrates in the processing module. Via the mounts, the processed specimen devices or substrates can be separated from the processing module. At least one of the processed specimen devices or substrates may comprise an optical microcuvette array, another may comprise a fluid-tight vial, another may comprise a transparent, reflective, or opaque microslide or cover glass, and one of the holding devices may comprise a dry film patch.

The specimen preparation unit may also have suitable waste chambers to contain all the liquid waste, and vents guarded with occlusive or absorptive valves to prevent the escape of any portion of the specimen or its processing fluids that are not needed for analysis. The chambers and vents, as well as the valves, may allow the specimen to pass stepwise through the processing channels without the escape of any portion of the specimen or processing fluids, including infectious organisms, into the environment outside the specimen preparation unit.

The centrifugal processing unit comprises a variable speed centrifuge with a multiply-armed rotor. An articulated socket is mounted at the end of each radial rotor arm. Centrifugal force is directed radially outward along each rotor arm when the rotor is activated. Each articulated socket is sized to receive and hold a single specimen preparation unit. Each articulated socket is associated with means for rotating the specimen preparation unit about a first axis and means for rotating the specimen preparation unit independently about a second, orthogonal axis. The axes of rotation of the articulated socket are perpendicular to each other and to the radial axis of its rotor arm, so as to allow the socket, and hence the specimen preparation unit, to be oriented freely in any possible orientation in relation to the centrifugal force vector. Rotation of the centrifuge and the mounting head may be accomplished by a pneumatically driven ratchet mechanism, by electromagnetic motor, or by other means known in the centrifuge art.

The specimen processing unit, by means of the centrifugal processing unit, specifically operates independently of the direction and extent of gravity, and, within the limits tolerable to human beings, independent of pressure.

The complete text of the claims presented herewith is hereby incorporated by reference into this specification as an illustrative description of some of the contemplated embodiments.

BRIEF DESCRIPTION OF THE DRAWINGS

FIGS. 2A and 2B are schematic representations of a generic specimen preparation unit during a multi-step processing cycle; views 2a-1, 2a-2, 2a-3, 2a-4, 2a-5, 2b-6, 2b-7, and 2b-8 shows the state of the unit after steps 1-8 in such a cycle.

FIG. 12 is a perspective drawing of the articulated rotor head of the centrifugal unit showing details of the socket indexing system.

DETAILED DESCRIPTION OF THE PREFERRED EMBODIMENTS

Figure 1:
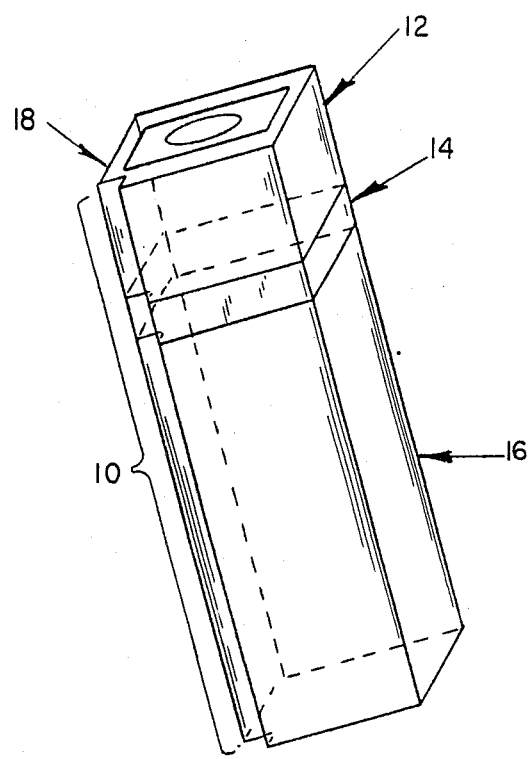
FIG. 1 is a schematic perspective view of the specimen preparation unit of the present invention showing its component modules.

With reference to FIG. 1, the specimen preparation unit 10 will be seen to comprise a collection module 12, an aliquoting module 14 and a processing module 16. The three modules are designed to stack on one another so that internal structures such as channels and chamber walls are in alignment. These modules are produced individually by plastic injection molding techniques and are ultrasonically welded to one another to form a monolithic elongated generally parallelepiped configuration 3.5 inches or less in length. One long edge of the unit thus formed embodies a longitudinal keyway 18 that orients and guides the specimen preparation unit 10 when it is inserted in the centrifugal processing unit shown in FIG. 11.

The collection module 12 initially receives a specimen to be prepared, the aliquoting module 14 measures out a predetermined amount of the specimen and stores premeasured quantities of diluents or initial reagents and the processing module 16 contains the reagents and physical substrates for the preparation of the specimen. The processing module 16 may contain one or more processing channels. Each channel in the processing module 16 embodies the appropriate substances and the devices for filtering, mixing, concentrating, washing, precipitating, incubating, etc. required to accomplish the preparation of the specimen for which each channel is adapted. At the completion of the processing cycle, accomplished automatically by means of the centrifugal processing unit seen in FIG. 11, the specimen or specimens are removed from the processing module 16, which retains all of its contents except the specimens.

Figure 11:
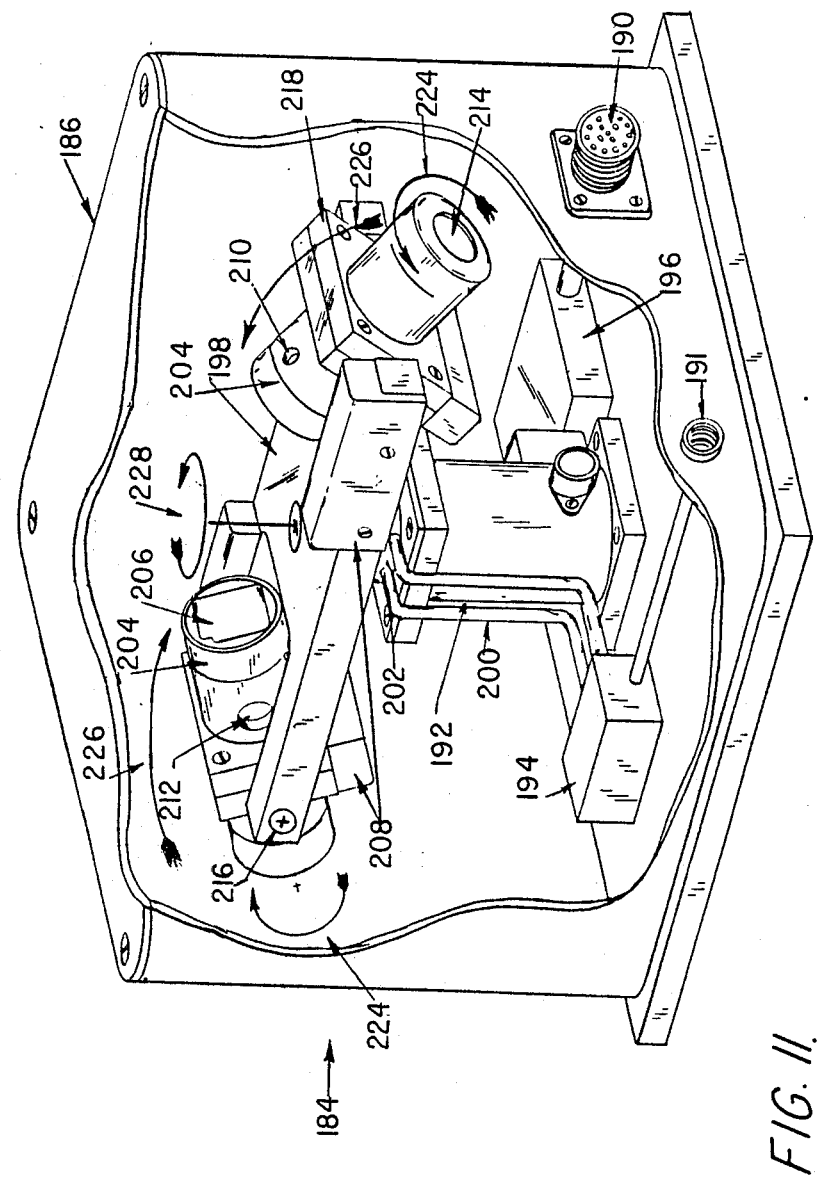
FIG. 11 is a perspective view of the centrifugal processing unit.

The centrifugal processing unit seen in FIG. 11 is designed to receive the specimen preparation unit 10 and apply centrifugal forces of specified strength and duration in a sequence of predetermined directions in order to provide the forces necessary for mixing, filtering, etc., in order for the processing module to carry out its function. The combination of internal configuration, appropriate valves, vents, internal waste chambers, etc. and the directed centrifugal force used to accomplish the processing cycle, allows the specimen preparation unit to function equivalently in the microgravity environment and the terrestrial gravity field.

Figures 1, 3A:
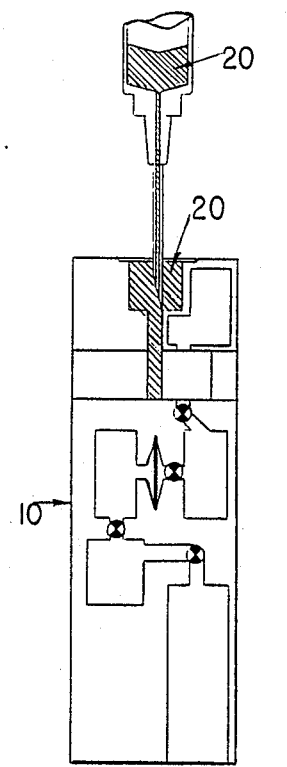
FIGS. 3A and 3B are schematic representations of a generic specimen preparation unit during a multi-step processing cycle yielding a prepared specimen in suspension in a sealed vial; views 3a-1, 3a-2, 3a-3, 3a-4, 3a-5, 3b-6, and 3b-7 show the state of the unit after steps 1-7 in this cycle.
Figures 2, 3A:
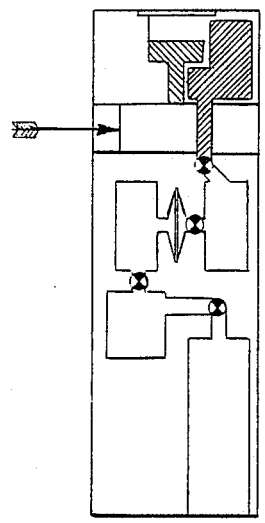
Figures 3, 3A:
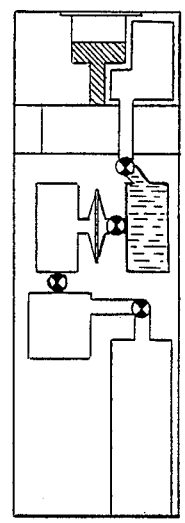
Figure 3A:
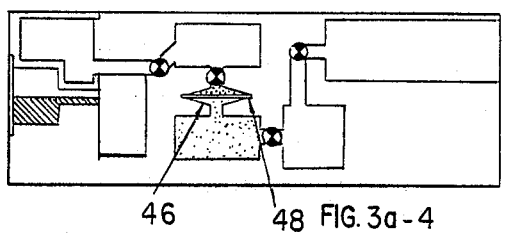

In FIGS. 2 and 3 two hypothetical specimen preparation cycles illustrate typical components of the specimen preparation unit 10 and the direction of sequential centrifugal forces as they would function to prepare a specimen that eventually resides on a microslide (FIG. 2) and in a sealed specimen vial (FIG. 3). The internal components of the specimen preparation units 10 depicted in FIGS. 2 and 3 represent miniaturized analogs of typical laboratory equipment. Along with others of similar generic character, these components can be assembled in endless ways, such that when subjected to the requisite pattern of directed centrifugal forces by the centrifugal processing unit, can accomplish different preparation routines on specimens of biologic or non-biologic character.

FIGS. 2A and 2B depict in schematic form, a typical specimen preparation cycle designed to prepare a cellular specimen, such as blood, on an optical slide for microscopic examination. Differing processing cycles, implying appropriately differing internal components in the specimen preparation unit 10 are appropriate for a wide class of specimen preparation procedures.

Step 1 (FIG. 2A): A specimen 20, such as blood, is installed in the chamber 22 of the collection module 12, filling the channel or manifold 24 and eventually the measuring chamber 26 in the aliquoting slide 28.

Step 2: The slide 28 is shifted to its alternative position (here to the right), aligning the measuring chamber 26 with the exit openings of the diluent chamber 30.

Step 3: The specimen preparation unit 10 is oriented by the centrifugal processing unit and spun so the centrifugal force flushes the diluent 32 through the measuring chamber 26, and with it, the specimen 20 past a one-way, pressure operated valve 33 that prevents reflux, and into the first processing chamber 34 of the processing module 16.

Step 4: The specimen preparation unit 10 is reoriented as shown in the figure and spun to drive the diluted specimen 36 into a delay chamber 38. The delay chamber 38 is included because in most specimen preparation unit 10 designs there are two or more parallel processing channels. In fact, in the usual instance, two processing routines like those shown in FIGS. 2 and 3 are embodied in the same specimen preparation unit. Since the two processing channels may require a different number of steps, delay chambers and one-way valves are needed to keep the two specimens moving in parallel with each succeeding reorientation and spin of the specimen preparation unit 10. Except for the passage of time, the contents of the delay chamber 38 are not processed in the delay step.

Step 5: The specimen preparation unit is reoriented and spun to move the diluted specimen 36 forward in its channel into the slide chamber 40.

Step 6 (FIG. 2B): The specimen preparation unit 10 is again reoriented to direct the centrifugal force perpendicular to the face of the microslide 42, and spun with sufficient force to precipitate cells or particles that may be in the diluted specimen 36 onto the surface of the microslide 42, where they adhere naturally or by means of an adhesive previously applied to the surface of the microslide 42.

Step 7: The specimen preparation unit 10 is reoriented and spun to force the supernatant portion of the diluted specimen 36 into the waste chamber 37, where said supernatant is trapped by a valve 33.

Step 8: The microslide 42, encased in a mount 43 with its specimen, is extracted from the specimen preparation unit 10, and the aliquoting slide 28 returned to its original position, sealing the processing channel to retrograde flow and completing the processing cycle.

In order to assure proper operation, three valves 33 must remain closed when subjected to the force of normal gravity, but open when subjected to a substantially greater force by centrifugal means. Preferably, the valves will remain closed even when the centrifugal acceleration is as much as two times gravity.

Figures 3, 3A, 4, 5:
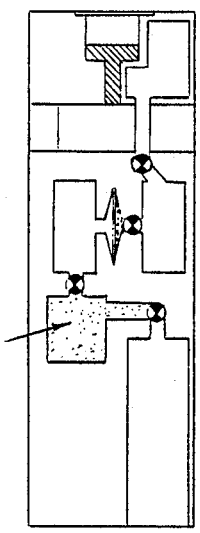
FIG. 4 is a perspective drawing of a generic collection module.
FIG. 5 is a perspective (5a) and plan (5b) drawing of a collection module designed to automatically collect a blood sample from a human fingertip.
Figures 3, 3B, 4, 5, 6:
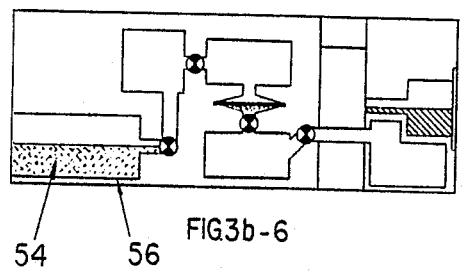
FIG. 6 is a perspective view of a generic two channel aliquoting module.

FIGS. 3A and 3B depict a second general type of processing cycle, in this instance delivering the processed specimen in a sealed vial. The processing cycle in FIG. 3 would be appropriate for separating particles or cells of two different sizes. In this example, the larger species of cell or particle is retained and discarded, and the smaller species of particle or cell is passed into the specimen vial for eventual analysis. For example, this type of processing cycle would be appropriate for the separation of the smaller platelets from the larger red and white blood cells in a specimen of human blood, or of bacteria from suspensions containing cells, debris, etc.

In the processing cycle depicted in FIG. 3A the first three steps are the same as those depicted in FIG. 2A, and could occur simultaneously in a second processing channel embodied in the same specimen preparation unit 10 as the processing cycle depicted in FIGS. 2A and B. By means of delay chambers, the remainder of the two processing cycles could also be accommodated in a singe specimen preparation unit 10.

Referring to FIG. 3A, after the specimen 20 has been aliquoted and flushed into the first chamber of this version of the specimen processing unit 10 the device is reoriented (step 4) and spun through a filter chamber 46 in which the filter 48 is sized to remove the larger species of cell or particle but allows the smaller particles to pass through.

The fifth step represents the movement of the filtrate into a delay chamber 38. In the sixth step (FIG. 3B) the fully prepared specimen 54 is transferred to the specimen vial 56. In the seventh step, the specimen vial 56 is extracted, and the aliquoting slide 28 is returned to its initial position, completing the hypothetical processing cycle represented in FIGS. 3A and 3B.

FIG. 4 represents a perspective drawing of one version of the collection module 12, designed to receive specimens from a standard syringe and needle. The entry port 58 to the specimen chamber 22 is covered by a rubber seal 60 held in place by a seal retainer 62. The specimen chamber 22 communicates with a manifold 24 that divides into the number of parallel specimen processing channels in the aliquoting module 14 and processing module 16. The manifold 24 ends in exit ports 64 that are aligned with sample entry ports 96 of the aliquoting module 14, seen in FIG. 6.

Among the variants of the collection module 12 are a version that aspirates a sample through a needle or small bore plastic catheter and a version that automatically collects a sample of capillary blood from a human fingertip. The automatic capillary blood sampler 66 is depicted in FIG. 5. This version of the collection module 12 contains a slide 72 with a cavity 74 large enough to admit a fingertip. A latch block 76 held in position with a spring 78 engages the first of two latch grooves 80 in the slide. The donor removes a tear off seal 68 covering the entry port 70 to reveal an elastic diaphragm 71. The elastic diaphragm 71 is deformed by mounting pressure from the fingertip until it ruptures. The rupture of the elastic diaphragm 71 causes the fingertip to suddenly fall on the latch block 76, releasing the slide 72. The movement of the slide 72 traps the fingertip against the edge of the entry port and also causes the stylet 84 to penetrate the side of the fingertip. Blood from the stylet wound is conducted into and through a channel or manifold 86 toward the aliquoting module 14. The second latch groove 80 prevents the slide 72 from excessive travel. When the sample has been successfully collected, the slide 72 may be manually pressed back to its original cocked position, releasing the fingertip.

A typical aliquoting module 14 is seen in perspective in FIG. 6. It consists of a main housing 90, a slide 28, a diluent reservoir assembly 92 and reservoir cover 94. The sample entry ports 96 are aligned with channels 98 that traverse the reservoir assembly 92 and are aligned with the upper orifices of the measuring chambers 26 in the slide 28. The lower orifices of the measuring chambers 26 are aligned with the vent ports 108. When the specimen is instilled into the collecting module 12, the manifold 24 conducts the specimen through the channels 98 that traverse the reservoir assembly 92 to fill the measuring chambers 26. When they are filled, the specimen passes via the vent ports 108 into a small vented chamber not shown in the figure. This arrangement insures the complete filling of the measuring chambers 26.

When the measuring chambers 26 are filled, the specimen preparation unit 10 is placed in the socket of the centrifugal processing unit seen in FIG. 11. There a device moves the aliquoting slide 28 to its alternate position via the actuating port 102. In this position, the measuring channels 26 in the aliquoting slide 28 are aligned with the diluent reservoir exit ports 110 seen in FIG. 7, and with the exit ports 106 that open into the processing module 16. The specimen preparation unit 10 is then oriented and spun to move the measured and diluted specimen aliquots into the processing module 16.

Figures 3, 3B, 4, 5, 6, 7:
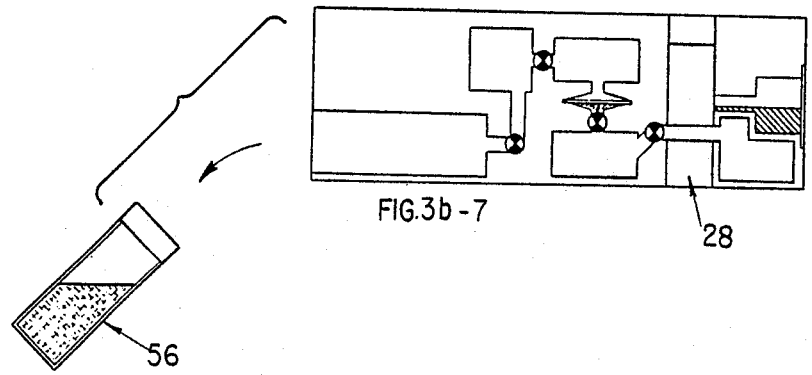
FIG. 7 is a plan (7a) and front elevational view of a typical two channel aliquoting module.
Figure 3B:
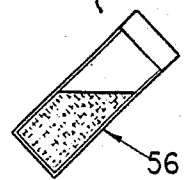
Figure 4:
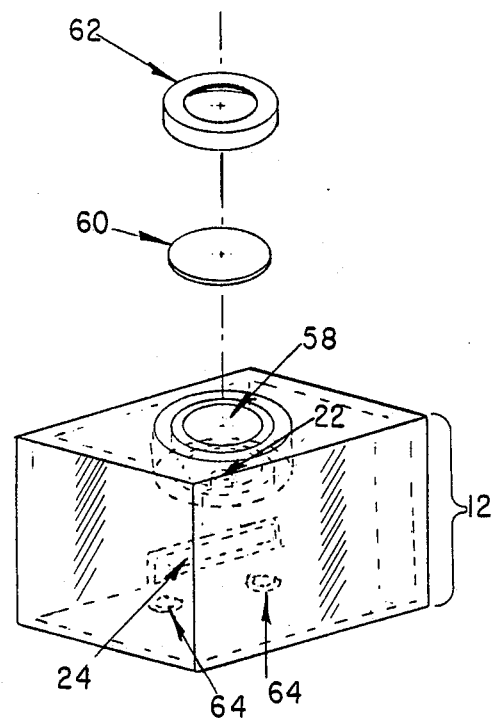

In FIG. 7 the same aliquoting module 14 is shown in plan and front elevation views to better illustrate the means by which the diluent reservoirs 100 are opened to release their contents into the measuring chambers 26 when the aliquoting slide 28 is moved to its alternate position. The reservoirs 100 are connected by diluent exit ports 110 to break off seals 112. Until these seals are broken, the diluents are confined to their reservoirs 100. The seals project into break off seal wells 104 in the aliquoting slide 28. When the aliquoting slide 28 is moved to its alternate position, the break off seals 112 are snapped off, opening the reservoirs to the measuring chambers 26. The aliquoting module 14 may have one, two, or more measuring chambers, as required by the processing module 16.

Figure 8:
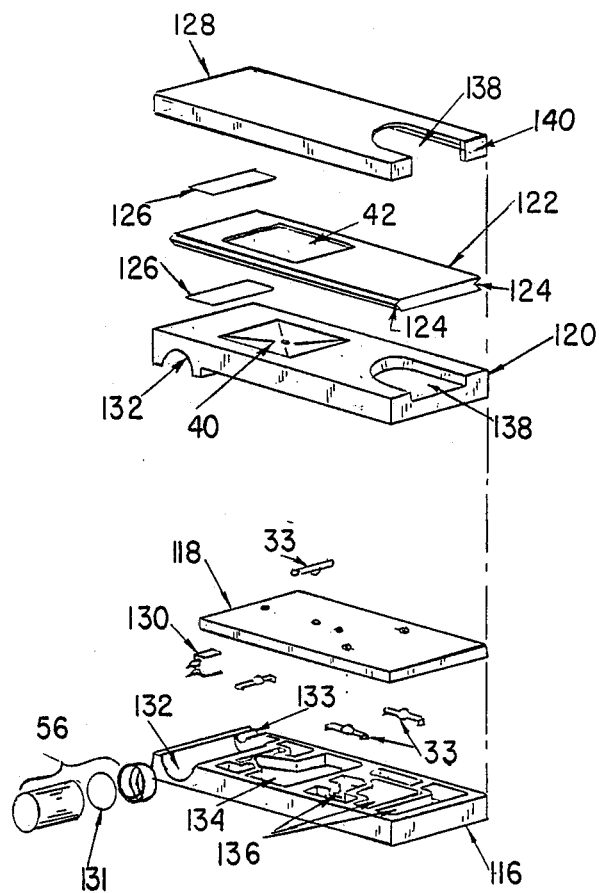
FIG. 8 is a perspective view of one typical embodiment of the processing module.

FIG. 8 depicts a typical dual channel processing module 16. The version shown corresponds closely with the schematic examples of processing modules 16 in FIGS. 2 and 3A and B, but embodied as parallel channels in a single processing module. It is designed to prepare a portion of the specimen on a microslide 42 for microscopic analysis, and another portion as a suspension delivered in the specimen vial 56. In the module in FIG. 8 a valve deck 118 separates the outer deck 116 from the inner deck 120. The valves 33 are disposed and structured to allow flow only in the directions required by the processing cycle. The chambers 136, and valves 33 are arranged in a complex fashion. The relationship of the major components can be appreciated in this view. The valve deck isolates the chambers in the inner deck 120 from the chambers in the outer deck 116. The large compartment in the outer deck 116 is a transfer chamber 134. The vial ejection port 133 will allow the eventual expulsion of the specimen vial 56 from its socket 132. The prepared specimen destined for the specimen vial 56 enters the vial through the fill/vent tube assembly 130. The two beveled tubes of the fill/vent assembly 130 penetrate the rubber diaphragm 131 of the specimen vial 56, which seals the vial as it is expelled by the specimen vial extractor (not shown) when said extractor projects through the vial extractor port 133.

The microslide 42 is housed in a universal slide mount 122. The universal slide mount 122 has suitable labels 126. The orienting bevels 124 allow it to slide into corresponding bevels in the slide retainer 128. At the end of the processing cycle, the universal slide mount 122 is extracted by the slide extractor (not shown) that extends into the slide extractor port 138 to grasp and remove the universal slide mount. The retaining tabs 140 are broken away in the process.

The valves 33 all function as one-way ("check") valves operated by an increased g-load produced by centrifugal force in the centrifugal processing unit depicted in FIG. 11. The valves not only prevent reflux but prevent the movement of any fluids within the specimen processing unit, except in response to directed forces greater than at least 2 g. Thus, the valves maintain the integrity of the processing module channels during manufacture, shipping, routine handling, etc. as well as during the processing cycle. In FIGS. 2 and 3 the valves 33 are represented schematically, and except for the break-off seals 112 seen in FIG. 7, the valves are preferably all of a hybrid ball/reed type as shown in FIGS. 6–9. However, the valves may be of any suitable type including double or single double reed valves, diaphragm valves, ball check valves, pore valves closed by surface tension, break-off (single use) valves or seals and valves that are variants of these types.

Figure 9:
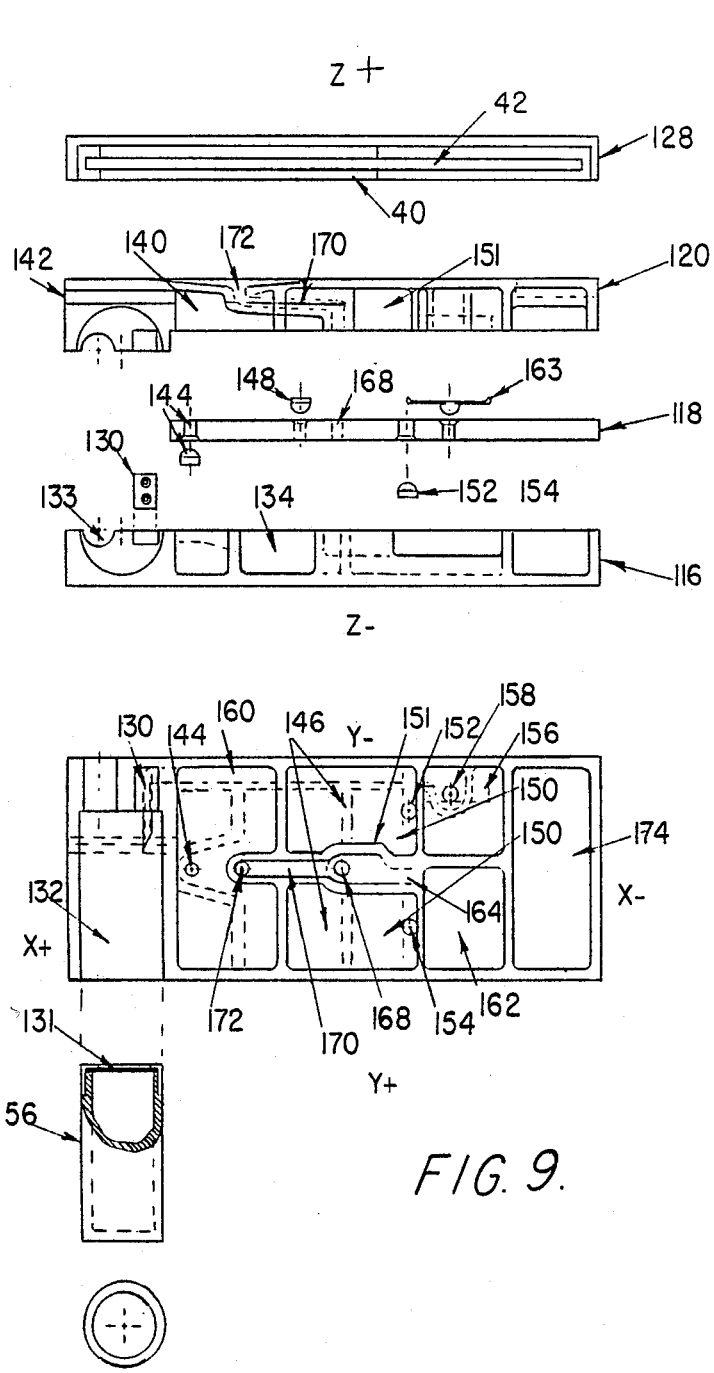
FIG. 9 is a front elevational and plan view of the processing module depicted in FIG. 8.

The plan and side elevation diagrams in FIG. 9 are used to describe the functioning of the version of the dual channel processing module 16 seen in FIG. 8. The slide retainer 128, the inner deck 120, the valve deck 118 and the outer deck 116 are seen in side elevation in the upper part of FIG. 9. The lower drawing in FIG. 9 is a plan view of all the decks superimposed. In the processing cycle described for this example of the processing module 16 the direction of the centrifugal force required in each processing step is referred to the labels X+, X−, Y+, Y−, Z+ and Z− that designate the six outer faces of the processing module 16.

After the aliquoting step (not shown in the diagram) the processing module 16 is oriented with the X− face down the centrifugal force vector and spun, moving the diluted specimen aliquot into the receiving chamber 141 via the entry channel 142. The diluted specimen may be incubated in the receiving chamber 141 for a variable period. At the end of incubation, the unit is reoriented with the Z− face down the centrifugal force vector and spun again, moving the specimen aliquot through the valve and channel at 144 into the transfer chamber 134. This step is necessary to position the specimen for the rest of the processing cycle. The unit is then reoriented to position the Z+ face down the centrifugal force vector and spun, moving the specimen through the channel and valve at 148 into the dividing chamber 146. The unit is again reoriented with the X− face down the centrifugal force vector and spun gently. The dividing chamber 146 has two volumetric wells 150 separated by a projection 151. The gentle spin partitions the aliquot, which just fills the wells 150 thereby dividing the specimen into two exact volumes. The rate of spin is then increased, opening the valves 152 and 154 and moving one volume into the vial transfer chamber 156, the other volume into the slide transfer chamber 162. The unit is then reoriented to position the Z− face down the centrifugal force vector and spun to move the vial specimen through the orifice 158 and valve at 163 into the vial transfer channel 160. During this latter spin the slide specimen remains trapped inside the slide transfer chamber 162. The unit is then reoriented to align the X+ face down the centrifugal force vector and spun, moving the vial specimen through the fill tube 130 into the specimen vial 56 and simultaneously moving the slide specimen through the transfer channel 164, then across the valve deck through the orifice at 168, through the continuation of the transfer channel 170, and finally through the orifice at 172 into the slide chamber 40. The specimen vial 56 is now extracted. Following the extraction of the specimen vial 56, the unit is reoriented with the Z+ face down the centrifugal force vector and spun vigorously to precipitate the particles or cells in the specimen onto the microslide 42. After this step the unit is reoriented and spun again to move the supernatant from the microslide specimen into the waste chamber 174. The valves 33 and channels to accomplish this were omitted from the drawings in FIG. 9 because the added complexity obscures the features described above. The microslide 42 with the specimen on its surface, is now extracted, ready for study.

Figure 10:
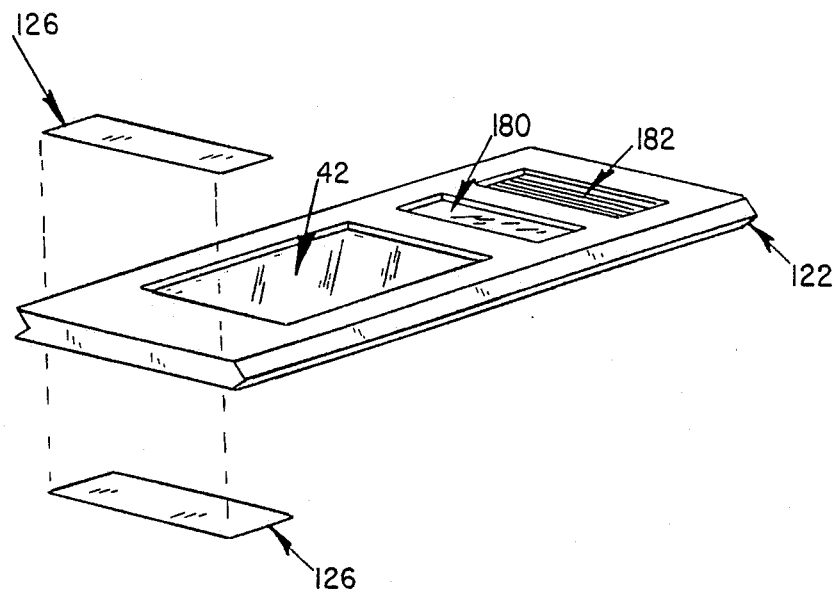
FIG. 10 is a perspective drawing of a typical version of a complex prepared specimen substrate for microscopic analysis.

FIG. 10 depicts an example of a more complex universal slide mount 122 for microscopic analysis. In this version, the universal slide mount 122 embodies the same labels 126 and microslide 42 illustrated in FIG. 8, but also includes two other options for presenting the specimen for analysis, namely a film patch 180 and a cuvette array 182. The film patch is a mosaic of smaller elements, each of which embodies the chemical substrates to combine with and quantitatively identify specific constituents of body fluids or other biologic, microbiologic, or non-biologic fluids. (The chemistry embodied in the film patch is not part of this application.) The cuvette array 182 consists of a variable number of microcapillary optical glass or transparent plastic tubes in a parallel array. The cuvettes may be individually preloaded with reagents that combine with and quantitatively identify specific constituents of body fluids, etc. as enumerated above. Each tube in the cuvette array can be analyzed by single or dual beam fluorescence, absorbance spectroscopy, or other means.

FIG. 11 is a perspective drawing representing the centrifugal processing unit 184. An explosion-proof enclosure 186 surrounds the centrifuge mechanism and serves to mount the socket for the electronic interface 190, an air supply interconnect 191, and loading and exit ports that automatically install the specimen preparation unit 10 in the centrifugal processing unit 184 and remove the prepared specimens. The loading and exit ports are not shown in FIG. 11. The enclosure is removably fastened to a base plate 188 that mounts the spin motor 192, the air valve unit 194 and the electronic unit 196. The electronic unit 196 responds to computer inputs to controls the function of the centrifugal processing unit 184.

The electronic unit 196 is based on a microprocessor, which receives computer instructions in standard form that correspond to the processing steps required by any of the variety of processing cycles embodied in the entire range of specimen preparation units 10. The computer instructions contain the starting and stopping positions of the rotor, the command for actuating the aliquoting slide 28, and the sequence of steps that constitute a particular processing cycle. Each step in the processing cycle includes the coordinates for positioning the specimen preparation unit socket 204, and the revolutions per minute and spin time required by each processing step. In addition to the microprocessor, the electronic unit embodies a tachometer, clock, and rotor position sensor that inform the microprocessor and the external computer of the rate and duration of spin and the exact angular location of the rotor 198. The electronic unit 196 also contains the circuitry for controlling the rate and duration of run of the spin motor 192, and the circuitry that signals the air valve unit 194.

The air valve unit 194 consists of sets of two electromagnetically or piezoelectrically operated air valves, one set of two valves for each of the positionable rotor heads. Each set is composed of one valve for the circumferential indexing mechanism 234 seen in FIG. 12, and one valve for the polar indexing mechanism 232, also seen in FIG. 12. Each air valve operates independently on signal from the electronic unit 196 to open for a short time (10 to 100 milliseconds) and then close, thus releasing a single pulse of air into a channel that connects with a particular indexing mechanism 208. That indexing mechanism 208 responds to a single pulse of air by rotating the socket 204 one increment in a circumferential direction 224 or polar direction 226. Each particular air valve and its corresponding indexing mechanism 208 are connected by a single channel consisting of air supply tube 200, a circumferential channel in the air distribution collar 202 that surrounds the drive shaft of the spin motor, and a channel in the rotor arm 198 that connects with the subject indexing mechanism. The air distribution collar 202 consists of a stationery outer sleeve and a closely inner fitting sleeve affixed to the rotor. The inner and outer sleeves contain a series of matching circumferential horizontal grooves that together form a series of parallel channels, one for each air valve-indexing mechanism assembly. Each sleeve also embodies a channel that connects a particular groove with its counterpart air supply tube (outer sleeve) or indexing mechanism channel (inner sleeve). This arrangement allows the controlled rotation of each socket independently to any three dimensional orientation with respect to the local direction vector of the centrifugal force generated by spinning the rotor. The indexing movements of the sockets 204 can occur with the motor at rest or in motion, depending on the needs of a particular processing cycle.

Each socket 204 embodies a socket cavity 206 into which a specimen preparation unit 10 can be placed. Each socket 204 also has an aliquoter actuation port 210, a vial extraction port 212 and a specimen preparation unit 10 ejection port 214. These ports admit moveable pins that perform the functions indicated by the names of the ports. The sockets 204 are suspended in the arms of the rotor 198 by trunions 216 and a trunion block 218. (The air driven indexing mechanisms 208 are seen in detail in FIG. 12.) By means of the indexing mechanisms 208, each socket 204 can be rotated inside its trunion block 218 in the direction shown by arrows 224, and independently rotated in the direction shown by arrows 226 by corresponding rotation of the trunion shaft 216. By means of rotation of the socket in the planes signified by arrows 224 and 226, the specimen preparation unit 10 can be placed in any possible orientation with respect to the centrifugal force produced by spinning the rotor 198 in the direction shown by arrow 228.

In use, the centrifugal processing unit 184 is controlled by a program that produces the specific processing routine required by a particular version of the specimen preparation unit 10. The processing cycle begins with the positioning of the rotor 198 with the socket at the loading port, ready to receive the specimen preparation unit 10. The specimen preparation unit 10 is loaded into the socket cavity 206 automatically by the loading port or by manual insertion. The rotor then moves the socket to the aliquoting station (not shown in the drawing) where an activating pin travels through the aliquoter activation port 210 to drive the aliquoting slide 28 (seen in FIGS. 6 and 7) to its alternative position. The indexing mechanisms then reposition the socket 204 and thus the specimen preparation unit 10 for the first processing step. The rotor is then spun to accomplish the first processing step. When the first spin is complete, the indexing mechanisms 208 then reorient the socket 204 and the second spin is carried out. This procedure is continued until the specimen is sequestered in the specimen vial 56 (providing the particular version of the specimen preparation unit 10 embodies a specimen vial 56). The rotor 198 is then positioned at the exit port (not shown in figure) where a specimen vial extractor pin (also not shown in the figure) pushes the specimen vial 56 out through the vial extraction port 212. The socket 204 is then again reoriented and the processing cycles continued until the microslide specimen is fully prepared. The rotor 198 then positions the socket 204 at the exit port where the slide extractor (not shown in figure) engages and removes the universal slide mount 122 from the specimen preparation unit 10. The rotor 1098 then returns the socket 204 to the aliquoting station, where the aliquoting slide 28 is returned to its original position, sealing the specimen channels. The socket 204 is then returned to the exit port and the specimen preparation unit 10 expelled by a pin that extends through the specimen preparation unit ejection port. The socket 204 is then reoriented and returned to the loading port ready to receive the next specimen preparation unit 10 to be processed.

In FIG. 11 the rotor assembly 204 is shown with two articulated heads. In practice, the number of rotor arms and heads can vary.

FIG. 12 depicts in perspective the detail of the articulated rotor head 230. The socket 204 is rotated in the two planes indicated in FIG. 11 by the action of the two indexing mechanisms 232 and 234. A circumferential gear 263 extends around the center of the socket 204. The circumferential gear 263 rests on a bearing flange 236 formed on the bottom trunion half 237. A similar flange is formed on the top trunion half 238. When the trunion block is assembled, the gear 263 is trapped between these two flanges except for a small opening through which the pawl 256 passes to move the socket incrementally in an axial direction when the axial indexing mechanism 234 is activated. Polar rotation is accomplished by a similar indexing mechanism 232 that operates on a racket wheel 252 that is affixed to one trunion pin. The polar indexing mechanism 232 consists of an actuating cylinder 250 which houses a piston 241, a pawl 242 and pawl spring 244, and a return spring 246, all held in place with a snap ring 248. The pawl 242 engages the rachet wheel 252 and moves it one gear tooth each time a pulse of air is delivered to the indexing mechanism 232. The axial indexing mechanism consists of similar parts and operates in a similar fashion. Again the actuating cylinder 262 contains a piston 254, pawl 256, return spring 258, and snap ring 260. The indexing mechanisms 232 and 234 thus engage the socket 204 and move it incrementally to orient the specimen preparation unit as desired.

The actuating cylinders 250 and 262 communicate with the air pressure source through air channels embodied in the rotor side rails 264. These in turn communicate with a similar number of channels that traverse the drive shaft of the spin motor 192 seen in FIG. 11. These channels communicate in turn with distribution grooves embodied in the air distribution collar 202. Each distribution groove communicates with an air line 200 that communicates with a valve in the air valve unit 194. Thus the operation of a particular air valve by computer signal produces the rotation of the socket 204 by one increment in the desired direction. By this means, the orientation of the socket 204 to position the proper face of the specimen processing unit 10 in the direction of centrifugal force can be accomplished by computer instruction.

The foregoing description is intended to illustrate the present invention but not to limit its scope or detail. Accordingly, numerous additions, substitutions and other modifications can be made without departing from the scope of the invention as set forth in the appended claims.

| LEGEND | |
| --- | --- |
| 10 specimen preparation unit | 141 receiving chamber |
| | 142 entry channel |
| 12 collection module | 144 valve and channel |
| 14 aliquoting module | 146 dividing chamber |

LEGEND

| # | Description | # | Description |
|---|---|---|---|
| 16 | processing module | 148 | channel and valve |
| 18 | longitudinal keyway | 150 | volumetric wells |
| 20 | specimen | 151 | projection |
| 22 | receiving chamber | 152 | valve |
| 24 | channel or manifold | 154 | valve |
| 26 | measuring chamber | 156 | vial transfer chamber |
| 28 | aliquoting slide | 158 | orifice |
| 30 | diluent chamber | 160 | vial transfer channel |
| 32 | diluent | 162 | slide transfer chamber |
| 33 | one-way valve | 163 | valve |
| 34 | processing module | 164 | transfer channel |
| 36 | diluted specimen | 168 | orifice |
| 37 | waste chamber | 170 | transfer channel continuation |
| 38 | delay chamber | | |
| 40 | slide chamber | 172 | orifice |
| 42 | microslide | 174 | waste chamber |
| 43 | slide mount | 180 | film patch |
| 54 | fully prepared specimen | 182 | cuvette array |
| 56 | specimen vial | 184 | centrifugal processing unit |
| 58 | entry port | | |
| 60 | rubber seal | 186 | enclosure |
| 62 | seal retainer | 188 | base plate |
| 64 | exit port | 190 | electronic interface |
| 66 | blood sample | 191 | air supply interconnect |
| 68 | seal | 192 | spin motor |
| 70 | entry port | 194 | air valve unit |
| 71 | diaphragm | 196 | electronic unit |
| 72 | slide | 198 | rotor |
| 74 | cavity | 200 | supply tube |
| 76 | latch block | 202 | air distribution collar |
| 78 | spring | 204 | sockets |
| 80 | latch grooves | 206 | socket cavity |
| 84 | stylet | 208 | indexing mechanism |
| 86 | manifold | 210 | aliquot actuation port |
| 90 | main housing | 212 | vial extraction port |
| 92 | diluent reservoir assembly | 214 | ejection port |
| | | 216 | trunion shaft |
| 94 | reservoir cover | 218 | trunion block |
| 96 | sample entry ports | 224 | arrow-axial rotation |
| 98 | channels | 226 | arrow-polar rotation |
| 100 | diluent reservoirs | 228 | arrow-rotor motion |
| 102 | actuating ports | 230 | articulated rotor head |
| 104 | seal break-off wells | 232 | indexing mechanism, polar |
| 106 | exit ports | 234 | indexing mechanism, axial |
| 108 | vent ports | 236 | bearing flange |
| 110 | diluent exit ports | 237 | bottom trunion half |
| 112 | break-off seals | 238 | top trunion half |
| 116 | outer deck | 241 | piston |
| 118 | valve deck | 242 | panel |
| 120 | inner deck | 244 | pawl spring |
| 122 | universal slide mount | 246 | return spring |
| 124 | orienting bevels | 248 | snap ring |
| 126 | labels | 250 | actuating cylinder |
| 128 | slide retainer | 252 | ratchet wheel |
| 130 | fill/vent tube assembly | 254 | piston |
| 132 | vial socket | 256 | panel |
| 133 | vial extractor port | 258 | return spring |
| 134 | transfer chamber | 260 | snap ring |
| 136 | chambers | 262 | actuating chamber |
| 138 | slide extractor port | 263 | circumferential gear |
| 140 | retaining tabs | 264 | rotor side rails |

I claim:

1. A centrifugal processing unit for directing the movement of substances within a specimen preparation unit having a plurality of compartments which comprises: (a) a rotor, (b) means for rotating said rotor to create a centrifugal force, said rotor having handling means for receiving a specimen preparation unit to whose contents the centrifugal force is applied and for rotating a specimen preparation unit about either or both of two axes orthogonal to each other and to the centrifugal force vector, into any selected orientation with respect to the direction of the centrifugal force applied by the rotor; and (c) control means for accelerating and decelerating the rotor and for causing said handling means to rotate a specimen preparation unit about either or both of said orthogonal axes to a plurality of different non-parallel selected orientations with respect to the centrifugal force vector, in a desired sequence.

2. The apparatus of claim 1, said handling means comprising a plurality of radial rotor arms, each arm having socket means for releasably receiving a specimen preparation unit, said socket means having a first indexing means for rotating a specimen preparation unit about a first axis and a second indexing means for independently rotating a specimen preparation unit about a second axis, said first and second axes being perpendicular to each other and to the rotor arm, the first and second indexing means associated with each rotor arm being independently controllable by said control means.

3. An apparatus for the preparation and analysis of a specimen which comprises, in combination,
   (a) a centrifugal processing unit according to claim 1, and
   (b) a specimen preparation unit receivable by said centrifugal processing unit, having a plurality of compartments, said compartments being adapted to hold a specimen and substances necessary for the preparation of analysis of the specimen; and means for controlling the flow of fluid between predetermined compartments when centrifugal force exceeding a local force of gravity is applied to the specimen preparation unit in particular directions, but restricting the flow of fluid between said compartments under local gravitational force, the complete preparation and analysis of the specimen requiring the flow of fluid in a plurality of nonparallel directions.

4. The centrifugal processing unit of claim 1, further comprising means for rotating the rotor to one or more predetermined positions.

5. The apparatus of claim 2, wherein the specimen preparation unit is releasably received by the second indexing means, and said first indexing means comprises first and second trunion means connected to each of said rotor arms and a trunion shaft held by said trunion means, said trunion shaft being connected to the second indexing means, such that the second indexing means is free to rotate about said trunion shaft between said first and second trunion means.

6. The apparatus of claim 5, wherein the second indexing means comprises a trunion block means and a socket having a socket cavity for receiving the specimen preparation unit, said trunion block means having a cavity for receiving the socket, said socket being capable of rotating inside the cavity of said trunion block means, the axis of said rotation being orthogonal to the axis of the trunion shaft.

* * * * *